(12) United States Patent
Wang et al.

(10) Patent No.: US 12,216,188 B2
(45) Date of Patent: Feb. 4, 2025

(54) METHOD AND APPARATUS FOR LIMITING RADIO FREQUENCY ALTERNATING MAGNETIC FIELD IN MAGNETIC RESONANCE IMAGING

(71) Applicant: Siemens Healthcare GmbH, Erlangen (DE)

(72) Inventors: Ying Lun Wang, Shenzhen (CN); Qiu Yi Zhang, Shenzhen (CN); Zhi Bin Li, Shenzhen (CN)

(73) Assignee: Siemens Healthineers AG, Erlangen (DE)

( * ) Notice: Subject to any disclaimer, the term of this patent is extended or adjusted under 35 U.S.C. 154(b) by 123 days.

(21) Appl. No.: 18/126,509

(22) Filed: Mar. 27, 2023

(65) Prior Publication Data
US 2023/0305091 A1 Sep. 28, 2023

(30) Foreign Application Priority Data
Mar. 28, 2022 (CN) .......................... 202210310391.1

(51) Int. Cl.
*G01R 33/565* (2006.01)
*A61B 5/055* (2006.01)
*G01R 33/28* (2006.01)
*G01R 33/34* (2006.01)
*G01R 33/341* (2006.01)

(52) U.S. Cl.
CPC ....... *G01R 33/5659* (2013.01); *G01R 33/288* (2013.01); *G01R 33/34015* (2013.01); *G01R 33/341* (2013.01); *A61B 5/055* (2013.01)

(58) Field of Classification Search
CPC ........................... A61B 5/055; G01R 33/288; G01R 33/34015; G01R 33/341; G01R 33/5659
See application file for complete search history.

(56) References Cited

U.S. PATENT DOCUMENTS

| | | | |
|---|---|---|---|
| 8,717,019 B2 * | 5/2014 | Ookawa | A61B 5/055 324/307 |
| 9,989,617 B2 * | 6/2018 | Nistler | G01R 33/586 |
| 10,598,740 B2 * | 3/2020 | Takai | G01R 33/543 |

* cited by examiner

*Primary Examiner* — Gregory H Curran
(74) *Attorney, Agent, or Firm* — Banner & Witcoff Ltd.

(57) ABSTRACT

A method and apparatus are provided for limiting a B1 field used for magnetic resonance imaging (MRI). The techniques described herein reduce a waste of performance of the B1 field while ensuring patient safety and improving the MR imaging quality.

10 Claims, 9 Drawing Sheets

Obtain a first intensity of a B1 field

Obtain a second intensity of the B1 field

Obtain a third intensity of the B1 field

METHOD AND APPARATUS FOR LIMITING RADIO FREQUENCY ALTERNATING MAGNETIC FIELD IN MAGNETIC RESONANCE IMAGING

CROSS-REFERENCE TO RELATED APPLICATIONS

The present application claims priority to and the benefit of China patent application no. CN 202210310391.1, filed on Mar. 28, 2022, the contents of which are incorporated herein by reference in their entirety.

TECHNICAL FIELD

The present disclosure relates to the technical field of magnetic resonance (MR) and, in particular, to a method and apparatus for limiting a radio frequency (RF) alternating magnetic field in magnetic resonance imaging (MRI), and an MR scanner.

BACKGROUND

The IEC standard for medical electrical equipment stipulates that during an MR scan, a surface temperature of a local coil placed on the part of the body being scanned must remain under 41° C. at the RF power to prevent injury to the body. However, this standard does not specify which method should be used to meet this requirement.

National Electrical Manufacturers Association (NEMA) MS-14 is a new standard, which provides a detailed description of an RF heating test for evaluating the safety of an MR local coil. Because the new MS-14 test standard requires a surface temperature of a local coil to be measured when a thermal equilibrium is reached, an RF alternating magnetic field, that is, a B1 field, generated by an RF coil must be limited and monitored more strictly such that RF coils that comply with the old standards still comply with the new standard.

At present, B1 fields of most MR scanners are limited based on a specific absorption rate (SAR) of a patient or a surface heating angle of an RF coil. In this case, an intensity of the B1 field is usually limited to a very low value, such that a surface temperature of a local coil does not exceed 41° C. even if a scanning duration is very long. However, in practical applications, scanning durations for scanning of most patients are limited. In this case, if the intensity of the B1 field is set to be too low, the performance of the B1 field may be wasted. It is proved through experiments that if the intensity of the B1 field is set to a corresponding intensity that enables the surface temperature of the coil to not exceed a regulatory requirement of 41° C., a scanning duration of 20 minutes may cause a loss of 1−(1/1.78)=43.8% in the performance of the B1 field, and a scanning duration of 10 minutes may cause a loss of 66.2% in the performance of the B1 field.

SUMMARY

In view of this, embodiments of the present disclosure propose a method and apparatus for limiting a B1 field in MR imaging to improve the MR imaging quality and to reduce waste of performance of the B1 field while ensuring patient safety under the condition that the total MR scanning duration is limited.

The embodiments of the present disclosure further propose an MR scanner to improve the MR imaging quality and to reduce a waste of performance of the B1 field while ensuring patient safety under the condition that the total MR scanning duration is limited.

The technical solution of the embodiments of the present disclosure is implemented as follows:

A method for limiting an RF alternating magnetic field (B1 field) in MRI, comprising:
  obtaining a first intensity of the B1 field that is required for a thermal equilibrium temperature of a surface temperature of a local coil to be a maximum safety temperature when the local coil is placed at a set position in an inspection bore of an MR scanner;
  obtaining, based on the first intensity of the B1 field and a relationship between the surface temperature of the local coil and a scanning duration and an intensity of the B1 field during an MR scanning process, a second intensity of the B1 field that is required for the surface temperature of the local coil to increase by heating to the maximum safety temperature within a set total MR scanning duration when the local coil is placed at the set position; and
  determining, based on the second intensity of the B1 field, a third intensity of the B1 field that is required when MR scanning is performed for the set total MR scanning duration, where the third intensity of the B1 field is not greater than the second intensity of the B1 field.

The set position may be a highest point of an inner bore wall of the inspection bore of the MR scanner.

Before the obtaining of a first intensity of the B1 field that is required for a thermal equilibrium temperature of a surface temperature of a local coil to be a maximum safety temperature when the local coil is placed at a set position in an inspection bore of an MR scanner, the method further comprises:
  when the local coil is placed at the set position and the intensity of the B1 field is one µT, obtaining a temperature difference between the thermal equilibrium temperature of the surface temperature of the local coil and an initial temperature of the surface temperature of the local coil, and setting the temperature difference as a first temperature difference; and
  the obtaining of a first intensity of the B1 field that is required for a thermal equilibrium temperature of a surface temperature of a local coil to be a maximum safety temperature when the local coil is placed at a set position in an inspection bore of an MR scanner comprises:
  when the local coil is placed at the set position in the inspection bore of the MR scanner and the thermal equilibrium temperature of the surface temperature of the local coil is the maximum safety temperature, obtaining a temperature difference between the maximum safety temperature and the initial temperature of the surface temperature of the local coil, and setting the temperature difference as a second temperature difference; and
  dividing the second temperature difference by the first temperature difference, and using an obtained quotient as a squared value of the first intensity of the B1 field.

The relationship between the surface temperature of the local coil and a scanning duration and an intensity of the B1 field during an MR scanning process is:

$$T(t) = T0 + B1^2 * \Delta T * \left(1 - e^{-\frac{t}{\tau}}\right)$$

where t represents a current scanned duration, T(t) represents a current temperature of the surface temperature of the local coil, T0 represents an initial temperature of the surface temperature of the local coil, B1 represents the intensity of the B1 field, ΔT represents a temperature difference between the thermal equilibrium temperature of the surface temperature of the local coil and the initial temperature of the surface temperature of the local coil when the local coil is placed at the set position in the inspection bore of the MR scanner and the intensity of the B1 field is one µT, and τ represents a scanning duration required for the surface temperature of the local coil to reach 0.632ΔT when the local coil is placed at the set position in the inspection bore of the MR scanner and the intensity of the B1 field is one µT.

The obtaining of a second intensity of the B1 field that is required for the surface temperature of the local coil to increase by heating to the maximum safety temperature within a set total MR scanning duration when the local coil is placed at the set position includes:

$$(B1_{short})^2 = (B1_{infinite})^2 * \frac{1}{1 - e^{-\frac{t_{scan}}{\tau}}}$$

where $B1_{short}$ represents the second intensity of the B1 field, $B1_{infinite}$ represents the first intensity of the B1 field, and $t_{scan}$ represents the set total MR scanning duration.

The determining, based on the second intensity of the B1 field, of a third intensity of the B1 field that is required when MR scanning is performed for the set total MR scanning duration includes:
when only one scanning protocol is used within the set total MR scanning duration, using the third intensity of the B1 field as an intensity of the B1 field that corresponds to the scanning protocol.

The determining, based on the second intensity of the B1 field, a third intensity of the B1 field that is required when MR scanning is performed for the set total MR scanning duration includes:
when a plurality of scanning protocols are used within the set total MR scanning duration and a scanning duration for each scanning protocol is the same, using the third intensity of the B1 field as a sum of intensities of the B1 field that correspond to all the scanning protocols, where an intensity of the B1 field that corresponds to the $n^{th}$ scanning protocol is:

$$(B1_{protocoln})^2 = \left(\frac{1}{2}\right)^n * (B1'_{short})^2$$

where $B1_{protocoln}$ represents the intensity of the B1 field that corresponds to the $n^{th}$ scanning protocol, and $B1_{short}'$ represents the third intensity of the B1 field, where $1 \leq n \leq N$, and N represents a total number of scanning protocols used within the set total MR scanning duration.

The determining, based on the second intensity of the B1 field, of a third intensity of the B1 field that is required when MR scanning is performed for the set total MR scanning duration includes:
when a plurality of scanning protocols are used within the set total MR scanning duration and a scanning duration for each scanning protocol is not completely the same, using the third intensity of the B1 field as a sum of intensities of the B1 field that correspond to all the scanning protocols, where an intensity of the B1 field that corresponds to the $n^{th}$ scanning protocol is:

$$(B1_{protocoln})^2 = \frac{\left(\frac{1}{2}\right)^n * (B1'_{short})^2 * t_{single\_protocol}}{t_{protocoln}}$$

where $B1_{protocoln}$ represents the intensity of the B1 field that corresponds to the $n^{th}$ scanning protocol, $B1_{short}'$ represents the third intensity of the B1 field, $t_{single\_protocol}$ represents a set standard scanning duration for a single scanning protocol, and $t_{protocoln}$ represents an actual scanning duration for the $n^{th}$ scanning protocol, where $1 \leq n \leq N$, and N represents a total number of scanning protocols used within the set total MR scanning duration.

The determining, based on the second intensity of the B1 field, of a third intensity of the B1 field that is required when MR scanning is performed for the set total MR scanning duration includes:
when a plurality of different types of scanning sequences are used within the set total MR scanning duration, obtaining, through the following steps A and B, an intensity of the B1 field that is used for each scanning sequence:
A. performing initialization m=1, and calculating:

$$(B1\_limit_m)^2 = \min\left\{\left(\frac{1}{2}\right)^m * \left(B1_{B1_{single\_protocol}}\right)^2, (B1_{SAR\_limit})^2\right\}$$

where:

$$(B1_{single\_protocol})^2 = (B1_{infinite})^2 * \frac{1}{1 - e^{-\frac{t_{single\_protocol}}{\tau}}}$$

$$t_{allowed\_duration\_m} = \frac{(B1_{single\_protocol})^2}{(B1\_limit_m)^2} * t_{single\_protocol}$$

and calculating a maximum value $P_m$ that satisfies:

$$\sum_{p_m=1}^{p_m=P_m} t_{seq\_p_m} \leq t_{allowed\_duration\_m}$$

where the maximum value $P_m$ is the number of scanning sequences for which $B1\_limit_m$ is used as the intensity of the B1 field;
where:
$B1\_limit_m$ represents the $m^{th}$ intensity of the B1 field that is used during a current MR scanning process, $B1_{single\_protocol}$ represents an intensity of the B1 field that is for a single scanning protocol, $B1_{SAR\_limit}$ represents a preset limit value of the intensity of the B1 field, B infinite represents the first intensity of the B1 field, $t_{single\_protocol}$ represents a set standard scanning duration for a single scanning protocol, τ represents a scanning duration required for the surface temperature of the local coil to reach 0.632*(the thermal equilibrium temperature—an initial temperature of the surface temperature of the local coil) when the local coil is placed at the set position in the inspection bore of the MR scanner and the intensity of the B1 field is one μT, $t_{allowed\_duration\_m}$ represents an upper limit of a scanning duration for the $m^{th}$ intensity of the B1 field, $p_m$ represents a sequence number of the $p^{th}$ scanning sequence in all scanning sequences for which $B1\_limit_m$ is used as the intensity of the B1 field during the current MR scanning process, $P_m$ represents the number of scanning sequences for which $B1\_limit_m$ is used as the intensity of the B1 field during the current MR scanning process, and $t_{seq\_p_m}$ represents a scanning duration for the $p^{th}$ scanning sequence in all scanning sequences for which $B1\_limit_m$ is used as the intensity of the B1 field during the current MR scanning process;

B. letting m=m+1, and returning to step A until:

$\Sigma P_m \geq P$ where P represents a total number of scanning sequences used during the current MR scanning process.

An apparatus for limiting an RF alternating magnetic field in MRI, including:

a B1 field first-intensity obtaining module configured to obtain a first intensity of a B1 field that is required for a thermal equilibrium temperature of a surface temperature of a local coil to be a maximum safety temperature when the local coil is placed at a set position in an inspection bore of an MR scanner; and a B1 field second-intensity obtaining module configured to obtain, based on the first intensity of the B1 field and a relationship between the surface temperature of the local coil and a scanning duration and an intensity of the B1 field during an MR scanning process, a second intensity of the B1 field that is required for the local coil to be heated to the maximum safety temperature within a set total MR scanning duration when the local coil is placed at the set position; and determine, based on the second intensity of the B1 field, a third intensity of the B1 field that is required when MR scanning is performed for the set total MR scanning duration, where the third intensity of the B1 field is not greater than the second intensity of the B1 field.

An MR scanner, including the apparatus for limiting an RF alternating magnetic field in MR scanning described above.

According to the embodiments of the present disclosure, the MR imaging quality is improved and waste of performance of the B1 field is reduced while ensuring patient safety under the condition that the total MR scanning duration is limited.

BRIEF DESCRIPTION OF THE DRAWINGS

Preferred embodiments of the present disclosure are described in detail below with reference to the accompanying figures, to give those skilled in the art a clearer understanding of the abovementioned and other features and advantages of the present disclosure. In the figures.

The reference signs in the accompanying drawings are as follows:

| Reference sign | Meaning |
|---|---|
| 201-203 | Steps |
| S1-S5 | Change curves of a surface temperature of a local coil at different intensities of a B1 field that are obtained when MR scanning is performed at the different intensities of the B1 field |
| S1'-S5' | Respective fitted curves of S1-S5 |
| 41 | Change curve of a surface temperature of a local coil that is obtained when a total MR scanning duration is 35 minutes and the surface temperature of the local coil reaches a maximum safety temperature of 41° C. at the end of scanning |
| 42 | Change curve of a surface temperature of a local coil that is obtained when a total MR scanning duration is unlimited and a thermal equilibrium temperature of the surface temperature of the local coil is 41° C. |
| 90 | Apparatus for limiting a B1 field in MRI |
| 91 | B1 field first-intensity obtaining module |
| 92 | B1 field second-intensity obtaining module |

DETAILED DESCRIPTION OF THE DISCLOSURE

In order to clarify the object, technical solution, and advantages of the present disclosure, the present disclosure is explained in further detail below by way of embodiments.

To ensure patient safety to the greatest extent, it is usually expected to obtain a maximum intensity of a B1 field that allows a surface temperature of a local coil to not exceed a maximum safety temperature (41° C.) when a total MR scanning duration is unlimited.

Figure 1:
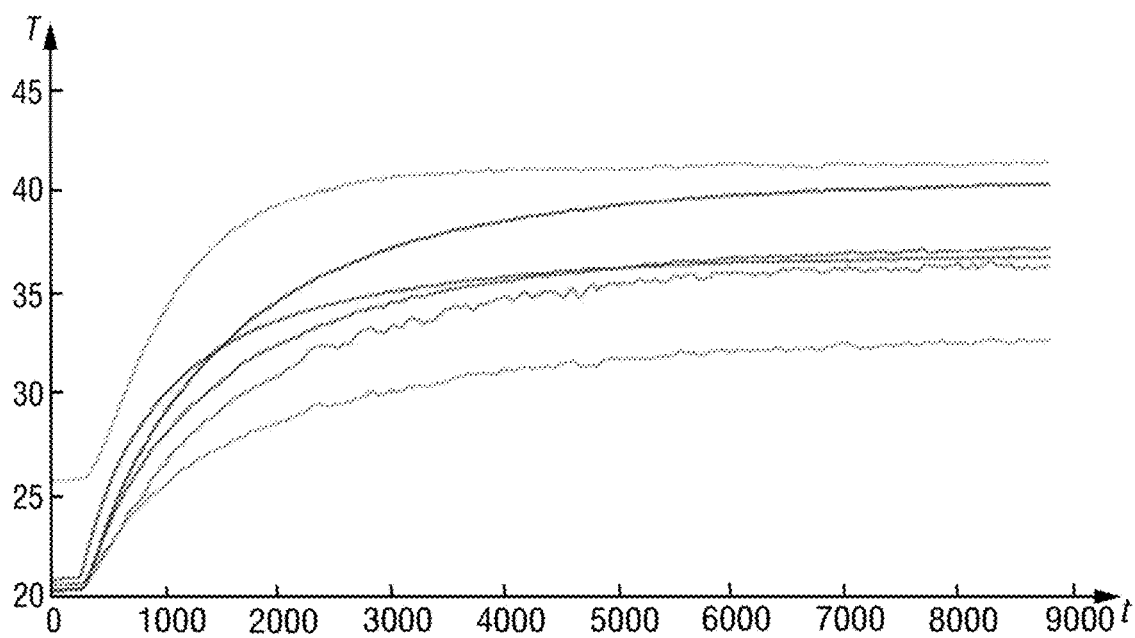
FIG. 1 is a schematic diagram of example change curves of a surface temperature of a local coil as a function of a scanning duration at different intensities of a B1 field, in accordance with an embodiment of the present disclosure.

FIG. 1 is a schematic diagram of example change curves of a surface temperature of a local coil as a function of a scanning duration at different intensities of a B1 field, in accordance with an embodiment of the present disclosure. It can be seen that when the total MR scanning duration is unlimited, the surface temperature of the local coil gradually increases as the scanning duration increases, but finally reaches a thermal equilibrium state (that is, the temperature remains substantially unchanged). In addition, it is known through experiments that, in the case of the same initial temperature of the surface temperature of the local coil, the greater the intensity of the B1 field, the higher the thermal equilibrium temperature that the surface temperature of the local coil finally reaches.

In addition, experiments show that it usually takes about 100 minutes for the surface temperature of the local coil to reach a thermal equilibrium state of 41° C. when the total MR scanning duration is unlimited. However, in practical applications, the total MR scanning duration is generally about 20 minutes. Therefore, within such total MR scanning duration, it is only necessary to ensure that the surface temperature of the local coil does not exceed the maximum safety temperature at the end of scanning. Therefore, in this case, the intensity of the B1 field may be increased.

Figure 2:
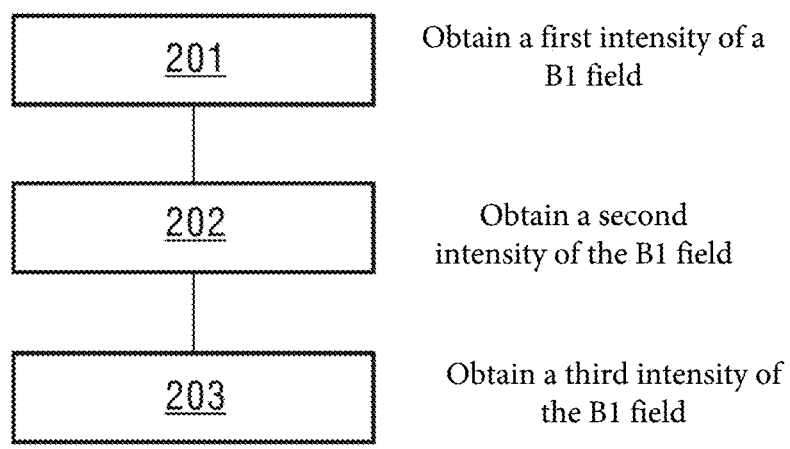
FIG. 2 is a flowchart of an example method for limiting a B1 field in MRI, in accordance with an embodiment of the present disclosure.

FIG. 2 is a flowchart of an example method for limiting a B1 field in MRI according to an embodiment of the present disclosure, where the method includes the following steps.

In step 201, a first intensity of the B1 field that is required for a thermal equilibrium temperature of a surface temperature of a local coil to be a maximum safety temperature when the local coil is placed at a set position in an inspection bore of an MR scanner is obtained.

During operation of the MR scanner, it can be found through analysis of intensity distribution of the B1 field in the inspection bore of the MR scanner that, the intensity of the B1 field is non-uniform along a vertical direction passing through the bore center of the inspection bore (that is, a direction passing through the bore center and perpendicular to the horizontal plane). Specifically, the intensity of the B1 field is the lowest at the bore center, the farther away from the bore center, the higher the intensity of the B1 field, and the intensity of the B1 field at the vertex of the bore wall (that is, the highest point of the bore wall of the inspection bore) is the highest. Therefore, the set position in step 201 may be the highest point of the inner bore wall of the inspection bore of the MR scanner.

In an optional embodiment, before step 201, the method further includes: when the local coil is placed at the set position and the intensity of the B1 field is one µT, obtaining a temperature difference between the thermal equilibrium temperature of the surface temperature of the local coil and an initial temperature of the surface temperature of the local coil, and setting the temperature difference as a first temperature difference.

Step 201 includes: when the local coil is placed at the set position in the inspection bore of the MR scanner and the thermal equilibrium temperature of the surface temperature of the local coil is the maximum safety temperature, obtaining a temperature difference between the maximum safety temperature and the initial temperature of the surface temperature of the local coil, and setting the temperature difference as a second temperature difference; and dividing the second temperature difference by the first temperature difference, and using an obtained quotient as a squared value of the first intensity of the B1 field.

In practical applications, the local coil is placed at the set position of the MR scanner, scanning is performed at different intensities of the B1 field to obtain change curves of the surface temperature of the local coil at the different intensities of the B1 field, and these change curves are fitted so as to obtain a relationship between the surface temperature of the local coil and a scanning duration and an intensity of the B1 field during an MR scanning process, which is as follows:

$$T(t) = T0 + B1^2 * \Delta T * \left(1 - e^{-\frac{t}{\tau}}\right) \quad (1)$$

where t represents a current scanned duration, i.e. a duration between a current moment and a starting moment of MR scanning, T(t) represents a current temperature of the surface temperature of the local coil, T0 represents an initial temperature of the surface temperature of the local coil, B1 represents the intensity of the B1 field, $\Delta T$ represents a temperature difference between the thermal equilibrium temperature of the surface temperature of the local coil and the initial temperature of the surface temperature of the local coil when the local coil is placed at the set position in the inspection bore of the MR scanner and the intensity of the B1 field is one µT, and τ represents a scanning duration required for the surface temperature of the local coil to reach $0.632\Delta T$ when the local coil is placed at the set position in the inspection bore of the MR scanner and the intensity of the B1 field is one µT.

Herein, assuming that an increasing degree of the surface temperature of the local coil has a linear relationship with a squared value of the intensity of the B1 field that is applied to the local coil, and a thermal resistance of the local coil remains unchanged during a heating process, a temperature increasing range obtained when the surface temperature of the local coil reaches a thermal equilibrium depends only on the power applied on the local coil or the squared value of the intensity of the B1 field. In addition, it is assumed that different powers applied to the local coil or the squared value of the intensity of the B1 field does not change a time constant, but depends only on a cooling condition.

Figure 3:
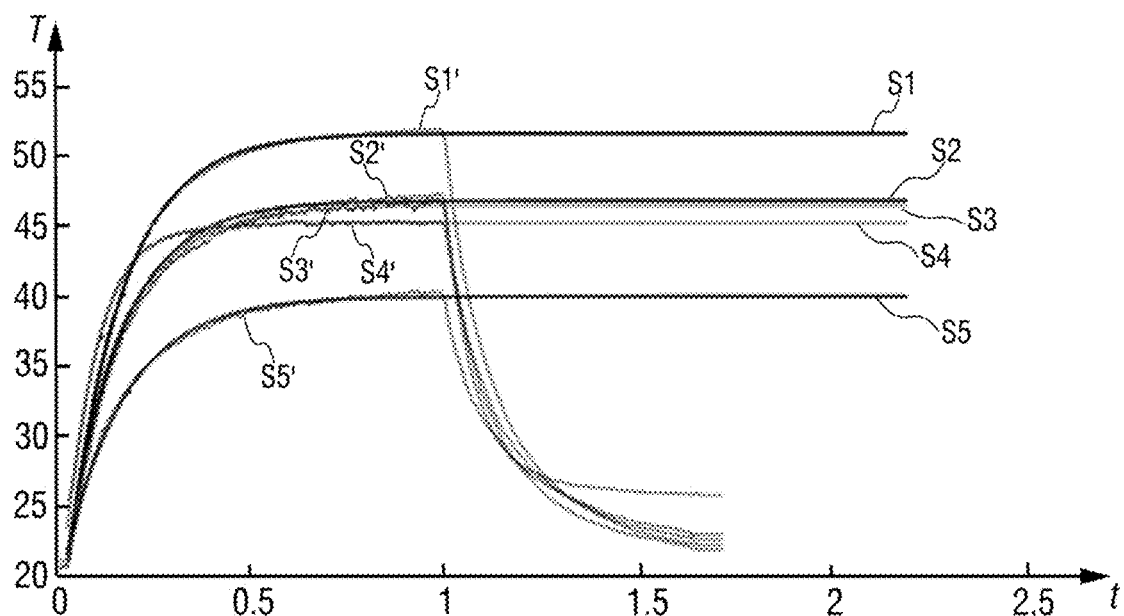
FIG. 3 is a schematic diagram of example change curves of a surface temperature of a local coil at different intensities of a B1 field that are obtained when MR scanning is performed at the different intensities of the B1 field and respective fitted curves of the change curves, in accordance with an embodiment of the present disclosure.

FIG. 3 is a schematic diagram of example change curves S1-S5 of a surface temperature of a local coil at different intensities of a B1 field that are obtained when MR scanning is performed at the different intensities of the B1 field and respective fitted curves S1'-S5' of the change curves. In FIG. 3, the horizontal coordinate represents a scanning duration, in hours (h), and the vertical coordinate represents the surface temperature of the local coil, in ° C. Since an actual total scanning duration for MR scanning is always limited in practical applications, only a limited total scanning duration needs to be considered for curve fitting. Therefore, in FIG. 3, only curves within one hour are fitted, and those beyond one hour are not considered.

When the total MR scanning duration is unlimited, the local coil is placed at the set position in the inspection bore of the MR scanner, and the thermal equilibrium temperature of the surface temperature of the local coil is the maximum safety temperature $T_{safety}$ (for example, 41° C.), the following is obtained according to formula (1):

$$T(\infty) = T0 + (B1_{infinite})^2 * \Delta T * \left(1 - e^{-\frac{t(\infty)}{\tau}}\right) = T_{safety} \quad (2)$$

where $B1_{infinite}$ represents the corresponding intensity of the B1 field for the thermal equilibrium temperature of the surface temperature of the local coil to be the maximum safety temperature $T_{safety}$ when the local coil is placed at the set position in the inspection bore of the MR scanner, i.e. the first intensity of the B1 field in step 201.

The following is obtained according to formula (2):

$$(B1_{infinite})^2 = \frac{T_{safety} - T0}{\Delta T} \quad (3)$$

In step 202, a second intensity of the B1 field that is required for the surface temperature of the local coil to increase by heating to the maximum safety temperature within a set total MR scanning duration when the local coil is placed at the set position is obtained based on the first intensity of the B1 field and a relationship between the surface temperature of the local coil and a scanning duration and an intensity of the B1 field during an MR scanning process.

When the set total MR scanning duration is $t_{scan}$, to ensure patient safety, the condition that the surface temperature of the local coil does not exceed the maximum safety temperature $T_{safety}$ at the end of the scanning needs to be met, and the following is obtained according to formula (1):

$$T(t_{scan}) = T0 + (B1_{short})^2 * \Delta T * \left(1 - e^{-\frac{t_{scan}}{\tau}}\right) = T_{safety} \quad (4)$$

Where $t_{scan}$ represents the set total MR scanning duration, that is, a maximum scanning duration for which the scanning can be performed by using $B1_{short}$ as the intensity of the B1 field, and $B1_{short}$ represents the corresponding intensity of the B1 field for the surface temperature of the local coil to reach the maximum safety temperature $T_{safety}$ at the end of the scanning when the total MR scanning duration is $t_{scan}$ and the local coil is placed at the set position, i.e. the second intensity of the B1 field in step 202.

The following is obtained according to formula (4):

$$(B1_{short})^2 = \frac{T_{safety} - T0}{\Delta T * \left(1 - e^{-\frac{t_{scan}}{\tau}}\right)} \quad (5)$$

The following is obtained according to formula (3) and formula (5):

$$\frac{(B1_{short})^2}{(B1_{infinite})^2} = \frac{1}{1 - e^{-\frac{t_{scan}}{\tau}}} \quad (6)$$

Then:

$$(B1_{short})^2 = (B1_{infinite})^2 * \frac{1}{1 - e^{-\frac{t_{scan}}{\tau}}} \quad (7)$$

In step 203, a third intensity of the B1 field that is required when MR scanning is performed for the set total MR scanning duration is determined based on the second intensity of the B1 field, where the third intensity of the B1 field is not greater than the second intensity of the B1 field.

In the above embodiment, the first intensity of the B1 field that is required for the thermal equilibrium temperature of the surface temperature of the local coil to be the maximum safety temperature when the local coil is placed at the set position in the inspection bore of the MR scanner is first obtained, the second intensity of the B1 field that is required for the surface temperature of the local coil to increase by heating to the maximum safety temperature within the set total MR scanning duration when the local coil is placed at the set position is then obtained based on the first intensity of the B1 field and the relationship between the surface temperature of the local coil and the scanning duration and the intensity of the B1 field during the MR scanning process, and the third intensity of the B1 field that is required when MR scanning is performed for the set total MR scanning duration is determined based on the second intensity of the B1 field, where the third intensity of the B1 field is not greater than the second intensity of the B1 field. Therefore, the MR imaging quality is improved and waste of performance of the B1 field is reduced while ensuring patient safety under the condition that the total MR scanning duration is limited.

Figure 4:
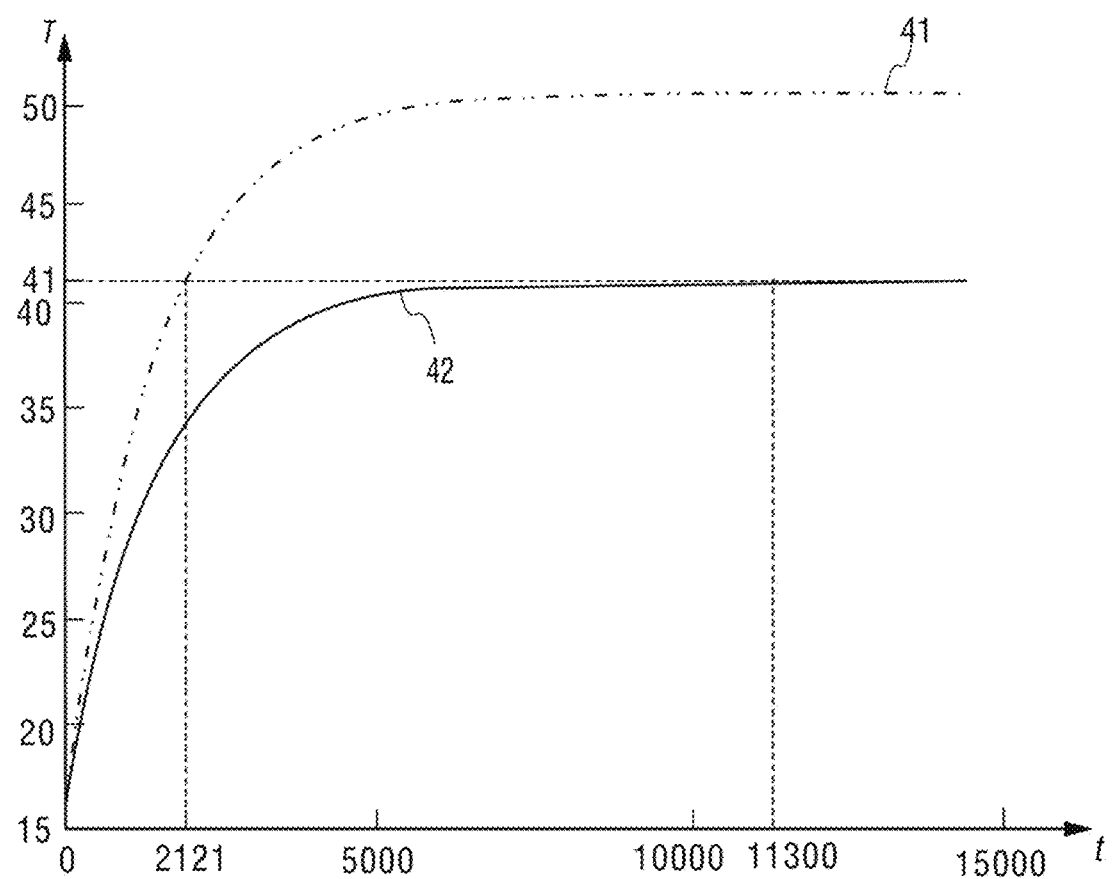
FIG. 4 is a schematic diagram of two example change curves of a surface temperature of a local coil in the case of τ=1454 seconds according to an embodiment of the present disclosure, where the first curve is obtained when a set total MR scanning duration is 35 minutes, and the surface temperature of the local coil reaches a maximum safety temperature of 41° C. at the end of the scanning, and the second curve is obtained when the total MR scanning duration is unlimited, and a thermal equilibrium temperature of the surface temperature of the local coil is 41° C.

FIG. 4 shows example change curves 41 and 42 of a surface temperature of a local coil in the case of τ=1454 seconds, where the first curve is obtained when a set total MR scanning duration is 35 minutes, and the surface temperature of the local coil reaches the maximum safety temperature of 41° C. at the end of the scanning, where it can be seen that when the scanning is performed for 2121 seconds (about 35 minutes), the surface temperature of the local coil reaches the maximum safety temperature of 41° C.; and the second curve is obtained when the total MR scanning duration is unlimited and the thermal equilibrium temperature of the surface temperature of the local coil is 41° C., where it can be seen that when the scanning is performed for 11300 seconds (about 188 minutes), the surface temperature of the local coil reaches the thermal equilibrium temperature of 41° C. In the figure, the horizontal coordinate represents the scanning duration, in seconds, and the vertical coordinate represents the surface temperature of the local coil, in ° C. The intensity of the B1 field that corresponds to the first curve 41 is greater than the intensity of the B1 field that corresponds to the second curve 42. Therefore, obviously, the quality of an MR image corresponding to the first curve 41 is higher.

Figure 5:
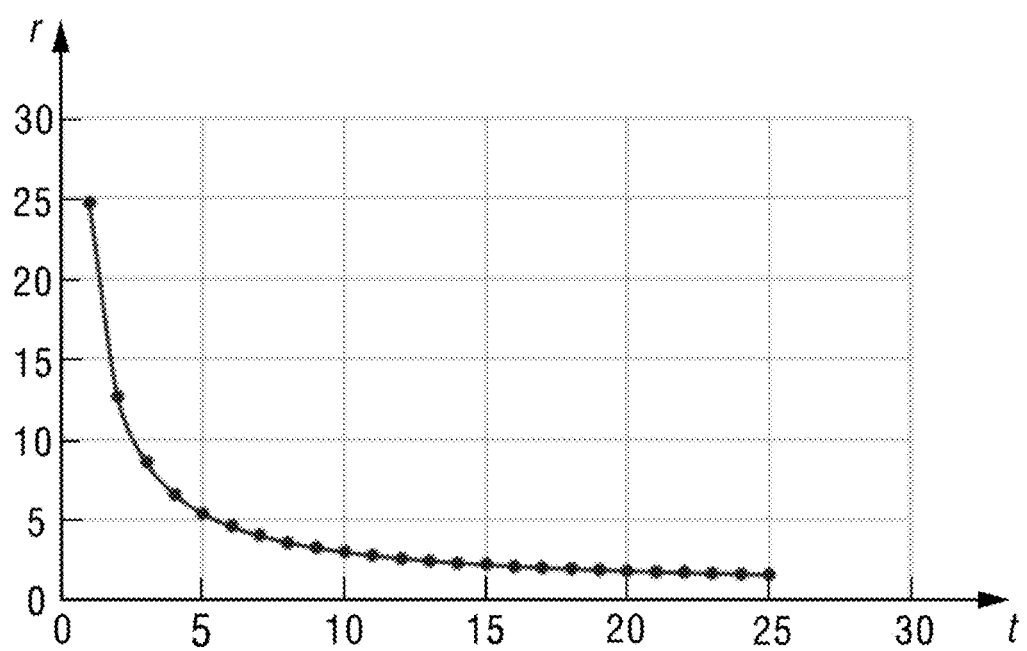
FIG. 5 is an example schematic diagram of a ratio r of ratio r of $(B1_{short})^2$ to $(B1_{infinite})^2$ that enables a surface temperature of a local coil to not exceed 41° C. within different limited total MR scanning durations when τ=1454 seconds according to an embodiment of the present disclosure.

FIG. 5 is a schematic diagram of a ratio r of $(B1_{short})^2$ to $(B1_{infinite})^2$ that enables the surface temperature of the local coil to not exceed 41° C. within different limited total MR scanning durations when τ=1454 seconds. In the figure, the horizontal coordinate represents a scanning duration, in minutes, and the vertical coordinate represents the ratio r of $(B1_{short})^2$ to $(B1_{infinite})^2$.

Table 1 shows specific values of the ratio of $(B1_{short})^2$ to $(B1_{infinite})^2$ that enables the surface temperature of the local coil to not exceed 41° C. within different limited total MR scanning durations when τ=1454 seconds.

TABLE 1

| τ (seconds) | Total MR scanning duration (minutes) | Ratio of $(B1_{short})^2$ to $(B1_{infinite})^2$ |
| --- | --- | --- |
| 1454 | 1 | 24.73677203 |
| | 2 | 12.62354347 |
| | 3 | 8.588091512 |
| | 4 | 6.572082249 |
| | 5 | 5.363848427 |
| | 6 | 4.559500576 |
| | 7 | 3.98594288 |
| | 8 | 3.556627144 |
| | 9 | 3.223470785 |
| | 10 | 2.957624028 |
| | 11 | 2.740727723 |
| | 12 | 2.560542253 |
| | 13 | 2.40859387 |
| | 14 | 2.278829744 |
| | 15 | 2.166810992 |
| | 16 | 2.069208321 |
| | 17 | 1.983475684 |
| | 18 | 1.907632709 |
| | 19 | 1.840115842 |
| | 20 | 1.779674147 |
| | 21 | 1.725294869 |
| | 22 | 1.67614931 |
| | 23 | 1.631552815 |
| | 24 | 1.59093477 |
| | 25 | 1.553815789 |

As shown in FIG. 5 and Table 1, when the total MR scanning duration is five minutes, and if the surface temperature of the local coil is required to reach 41° C. at the end of the five-minute scanning, $(B1_{short})^2=5.363848427*(B1_{infinite})^2$ used in this case is calculated.

When the total MR scanning duration is ten minutes, and if the surface temperature of the local coil is required to reach 41° C. at the end of the ten-minute scanning, $(B1_{short})^2=2.957624028*(B1_{infinite})^2$ used in this case is calculated.

In practical applications, one or more scanning protocols may be used in an MR scanning process.
(1) When only one scanning protocol is used within the set total MR scanning duration, the third intensity of the B1 field is used as an intensity of the B1 field that corresponds to the scanning protocol.
(2) When a plurality of scanning protocols are used within the set total MR scanning duration and a scanning duration for each scanning protocol is the same, the third intensity of the B1 field is used as a sum of intensities of the B1 field that correspond to all the scanning protocols, where an intensity of the B1 field that corresponds to the $n^{th}$ scanning protocol is:

$$(B1_{protocoln})^2 = \left(\frac{1}{2}\right)^n * (B1'_{short})^2$$

where $B1_{protocoln}$ represents the intensity of the B1 field that corresponds to the $n^{th}$ scanning protocol, and $B1_{short}'$ represents the third intensity of the B1 field, where $1 \leq n \leq N$, and N represents a total number of scanning protocols used within the set total MR scanning duration.

Figure 6:
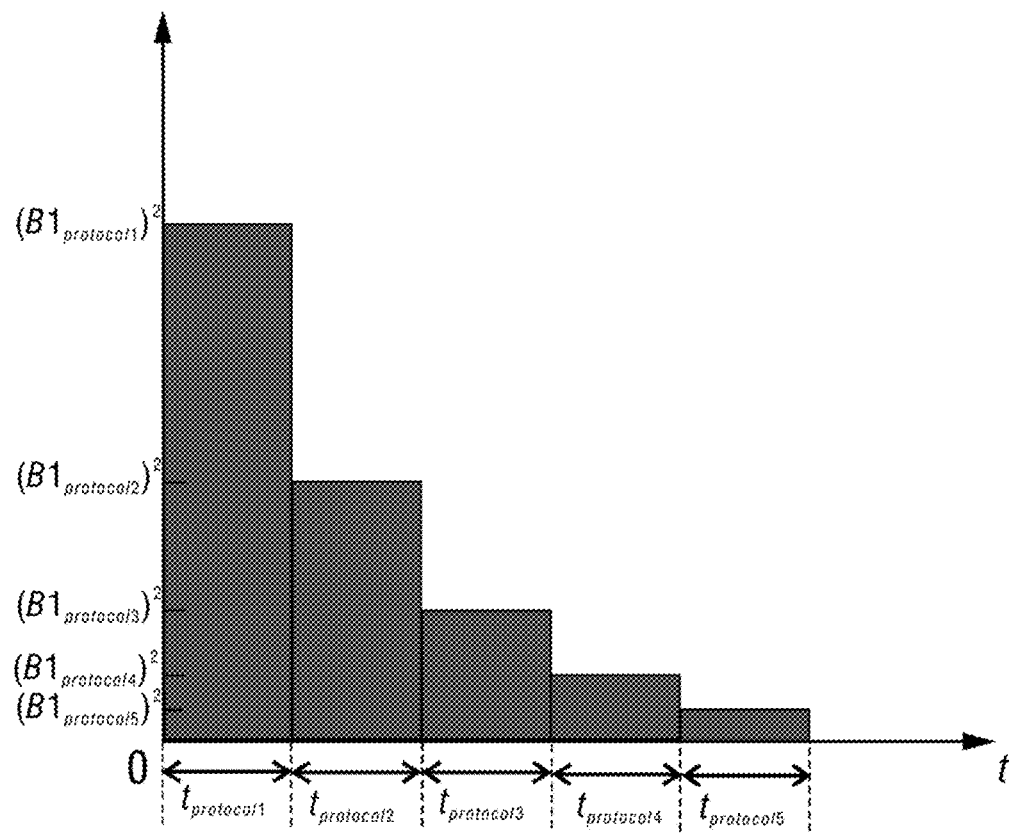
FIG. 6 is an example schematic diagram of intensities of a B1 field that respectively correspond to five scanning protocols used within a set total MR scanning duration according to an embodiment of the present disclosure, where a scanning duration for each scanning protocol is the same.

FIG. 6 is an example schematic diagram of intensities of the B1 field that respectively correspond to five scanning protocols used within the set total MR scanning duration, where a scanning duration for each scanning protocol is the same (that is, tprotocol1=tprotocol2=tprotocol3=tprotocol4=tprotocol5). In the Figure, the horizontal coordinate represents a scanning duration, and the vertical coordinate represents an intensity of the B1 field, where the intensity $B1_{protocol1}$ of the B1 field that corresponds to a scanning protocol 1 is:

$$(B1_{protocol1})^2 = \left(\frac{1}{2}\right) * (B1'_{short})^2$$

the intensity $B1_{protocol2}$ of the B1 field that corresponds to a scanning protocol2 is:

$$(B1_{protocol2})^2 = \left(\frac{1}{2}\right)^2 * (B1'_{short})^2$$

The rest may be deduced by analogy.
(3) When a plurality of scanning protocols are used within the set total MR scanning duration and a scanning duration for each scanning protocol is not completely the same, the third intensity of the B1 field is used as a sum of intensities of the B1 field that correspond to all the scanning protocols, where an intensity of the B1 field that corresponds to the $n^{th}$ scanning protocol is:

$$(B1_{protocoln})^2 = \frac{\left(\frac{1}{2}\right)^n * (B1'_{short})^2 * t_{single\_protocol}}{t_{protocoln}}$$

where $B1_{protocoln}$ represents the intensity of the B1 field that corresponds to the $n^{th}$ scanning protocol, $B1_{short}'$ represents the third intensity of the B1 field, $t_{single\_protocol}$ represents a set standard scanning duration for a single scanning protocol, and $t_{protocoln}$ represents an actual scanning duration for the $n^{th}$ scanning protocol, where $1 \leq n \leq N$, and N represents a total number of scanning protocols used within the set total MR scanning duration.

Figure 7:
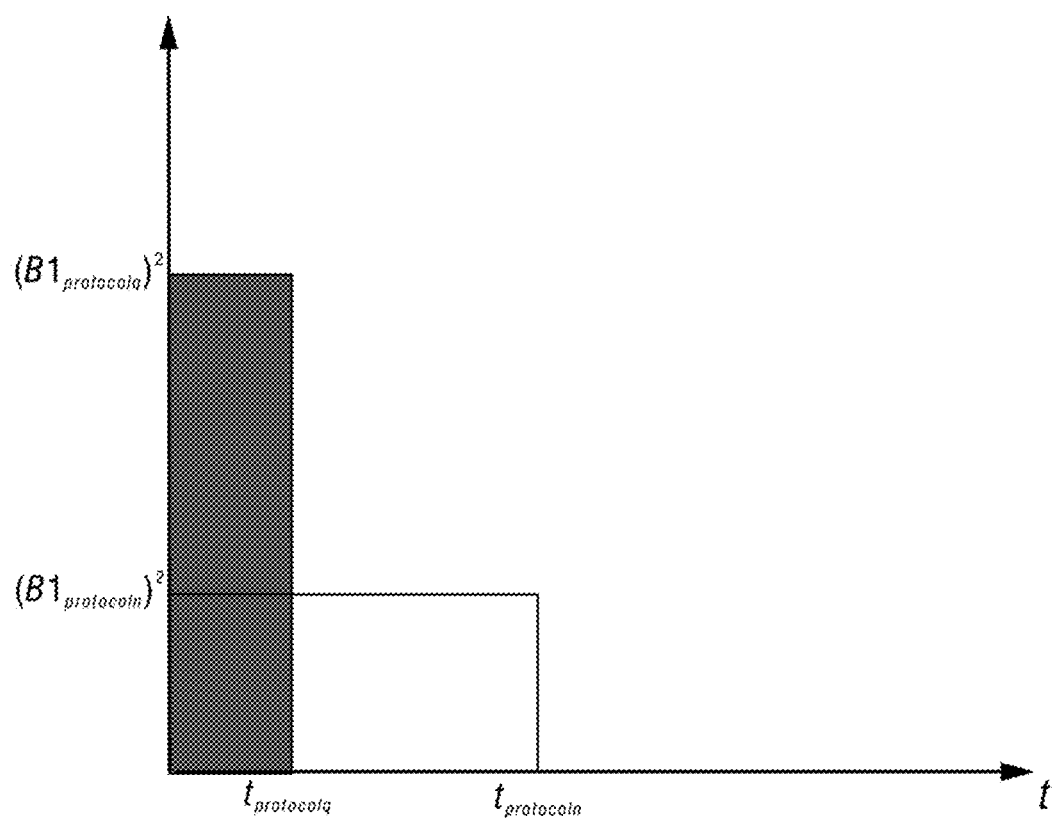
FIG. 7 is an example schematic diagram showing a comparison between an intensity of a B1 field that corresponds to the nth scanning protocol and an intensity of the B1 field that corresponds to the qth scanning protocol in a plurality of scanning protocols used within a set total MR scanning duration according to an embodiment of the present disclosure, where a scanning duration for each scanning protocol is not completely the same.

FIG. 7 is an example schematic diagram showing a comparison between an intensity $(B1_{protocoln})^2$ of the B1 field that corresponds to the $n^{th}$ scanning protocol and an intensity $(B1_{protocolq})^2$ of the B1 field that corresponds to the $q^{th}$ scanning protocol in a plurality of scanning protocols used within the set total MR scanning duration, where a scanning duration for each scanning protocol is not completely the same, the scanning duration $t_{protocoln}$ for the $n^{th}$ scanning protocol is not equal to $t_{single\_protocol}$, and the scanning duration $t_{protocolq}$ for the $q^{th}$ scanning protocol is equal to $t_{single\_protocol}$.
(4) When a plurality of different types of scanning sequences are used within the set total MR scanning duration, an intensity of the B1 field that is used for each scanning sequence is obtained through the following steps A and B:
A. performing initialization m=1, and calculating:

$$(B1\_limit_m)^2 = \min\left\{\left(\frac{1}{2}\right)^m * (B1_{single\_protocol})^2, (B1_{SAR\_limit})^2\right\}$$

where:

$$(B1_{single\_protocol})^2 = (B1_{infinite})^2 * \frac{1}{1 - e^{-\frac{t_{single\_protocol}}{\tau}}}$$

-continued $$t_{allowed\_duration\_m} = \frac{(B1_{single\_protocol})^2}{(B1\_limit_m)^2} * t_{single\_protocol}$$

and calculating a maximum value that satisfies:

$$\sum_{p_m=1}^{p_m=P_m} t_{seq\_p_m} \leq t_{allowed\_duration\_m}$$

where the maximum value $P_m$ is the number of scanning sequences for which $B1\_limit_m$ is used as the intensity of the B1 field;

where:

$B1\_limit_m$ represents the $m^{th}$ intensity of the B1 field that is used during a current MR scanning process, $B1_{single\_protocol}$ represents an intensity of the B1 field that is for a single scanning protocol, $B1_{SAR\_limit}$ represents a preset SAR-based limit value of the intensity of the B1 field, $B1_{infinite}$ represents the first intensity of the B1 field, $t_{single\_protocol}$ represents a set standard scanning duration for a single scanning protocol, τ represents a scanning duration required for the surface temperature of the local coil to reach 0.632*(the thermal equilibrium temperature—an initial temperature of the surface temperature of the local coil) when the local coil is placed at the set position in the inspection bore of the MR scanner and the intensity of the B1 field is one μT, $t_{allowed\_duration\_m}$ represents an upper limit of a scanning duration for the $m^{th}$ intensity of the B1 field, $p_m$ represents a sequence number of the $p^{th}$ scanning sequence in all scanning sequences for which $B1\_limit_m$ is used as the intensity of the B1 field during the current MR scanning process, $P_m$ represents the number of scanning sequences for which $B1\_limit_m$ is used as the intensity of the B1 field during the current MR scanning process, and $t_{seq\_p_m}$ represents a scanning duration for the $p^{th}$ scanning sequence in all scanning sequences for which $B1\_limit_m$ is used as the intensity of the B1 field during the current MR scanning process;

B. letting m=m+1, and returning to step A until:

$$\Sigma P_m \geq P$$

where P represents a total number of scanning sequences used during the current MR scanning process.

Figure 8:
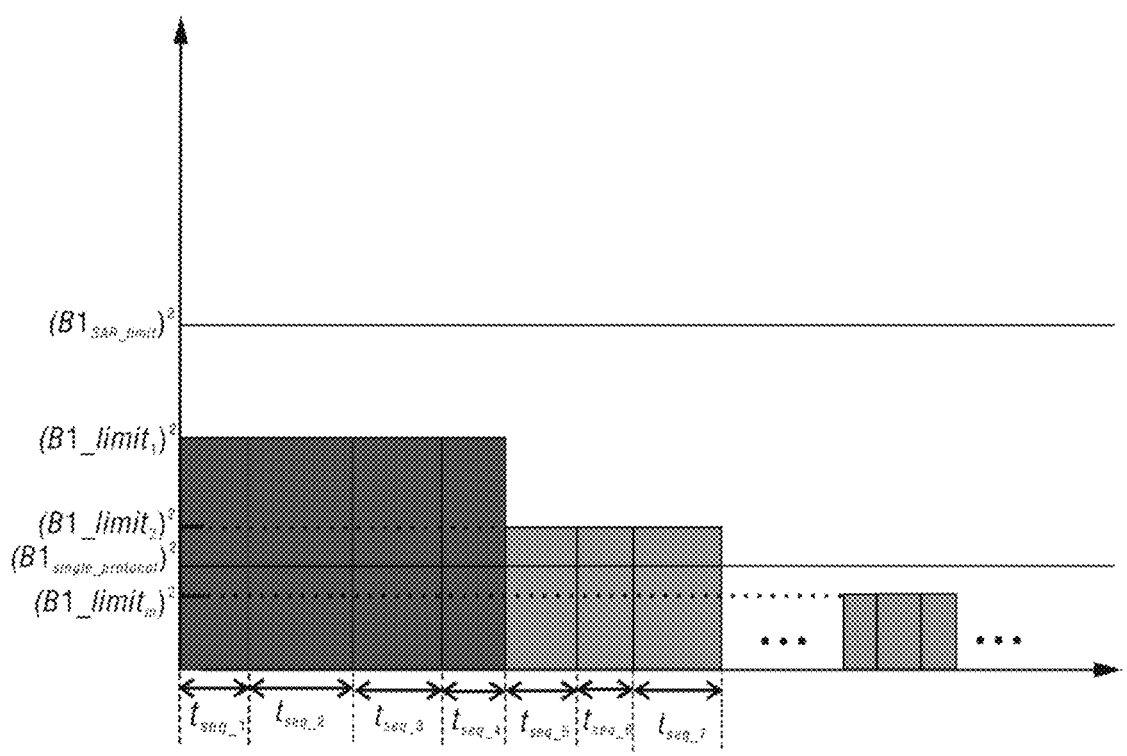
FIG. 8 is an example schematic diagram of intensities of a B1 field that respectively correspond to a plurality of different types of scanning sequences used within a set total MR scanning duration according to an embodiment of the present disclosure.

FIG. 8 is an example schematic diagram of intensities of a B1 field that respectively correspond to a plurality of scanning sequences used within a set total MR scanning duration. As shown in FIG. 8, $B1\_limit_1$ is used as the intensity of the B1 field for the first to fourth scanning sequences, and $B1\_limit_2$ is used as the intensity of the B1 field for the fifth to seventh scanning sequences, where a sum of scanning durations for the first to fourth scanning sequences is $t_{seq\_1}+t_{seq\_2}+t_{seq\_3}+t_{seq\_4} \leq t_{allowed\_duration\_1}$, and a sum of scanning durations for the fifth to seventh scanning sequences is $t_{seq\_5}+t_{seq\_6}+t_{seq\_7} \leq t_{allowed\_duration\_2}$.

Figure 9:
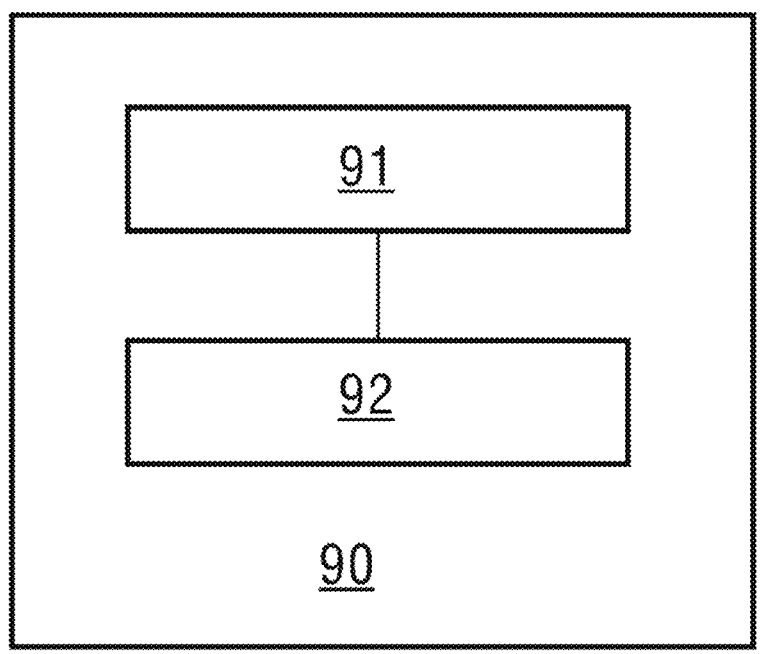
FIG. 9 is an example schematic structural diagram of an apparatus for limiting a B1 field in MRI according to an embodiment of the present disclosure.

FIG. 9 is an example schematic structural diagram of an apparatus 90 for limiting a B1 field in MRI according to an embodiment of the present disclosure. The apparatus 90 mainly includes a B1 field first-intensity obtaining module 91 and a B1 field second-intensity obtaining module 92. Although not shown in FIG. 9 for purposes of brevity, the apparatus 90 may additionally comprise any suitable number and/or type of processor, processing circuitry, etc., configured to execute computer-readable instructions stored in the modules 91, 92. By way of the execution of the computer-readable instructions stored in the respective modules 91, 92, any of the embodiments as discussed herein may be implemented.

The B1 field first-intensity obtaining module 91 is configured to obtain a first intensity of the B1 field that is required for a thermal equilibrium temperature of a surface temperature of a local coil to be a maximum safety temperature when the local coil is placed at a set position in an inspection bore of an MR scanner.

The B1 field second-intensity obtaining module 92 is configured to obtain, based on the first intensity of the B1 field and a relationship between the surface temperature of the local coil and a scanning duration and an intensity of the B1 field during an MR scanning process, a second intensity of the B1 field that is required for the local coil to be heated to the maximum safety temperature within a set total MR scanning duration when the local coil is placed at the set position; and determine, based on the second intensity of the B1 field, a third intensity of the B1 field that is required when MR scanning is performed for the set total MR scanning duration, where the third intensity of the B1 field is not greater than the second intensity of the B1 field.

In an optional embodiment, the set position in each of the B1 field first-intensity obtaining module 91 and the B1 field second-intensity obtaining module 92 is the highest point of an inner bore wall of the inspection bore of the MR scanner.

In an optional embodiment, before the obtaining, by the B1 field first-intensity obtaining module 91, of a first intensity of the B1 field that is required for a thermal equilibrium temperature of a surface temperature of a local coil to be a maximum safety temperature when the local coil is placed at a set position in an inspection bore of an MR scanner, the following step is further included: when the local coil is placed at the set position and the intensity of the B1 field is one μT, obtaining a temperature difference between the thermal equilibrium temperature of the surface temperature of the local coil and an initial temperature of the surface temperature of the local coil, and setting the temperature difference as a first temperature difference.

The obtaining, by the B1 field first-intensity obtaining module 91, of a first intensity of the B1 field that is required for a thermal equilibrium temperature of a surface temperature of a local coil to be a maximum safety temperature when the local coil is placed at a set position in an inspection bore of an MR scanner includes: when the local coil is placed at the set position in the inspection bore of the MR scanner and the thermal equilibrium temperature of the surface temperature of the local coil is the maximum safety temperature, obtaining a temperature difference between the maximum safety temperature and the initial temperature of the surface temperature of the local coil, and setting the temperature difference as a second temperature difference; and dividing the second temperature difference by the first temperature difference, and using an obtained quotient as a squared value of the first intensity of the B1 field.

In an optional embodiment, the relationship, on which the B1 field second-intensity obtaining module 92 is based, between the surface temperature of the local coil and a scanning duration and an intensity of the B1 field during an MR scanning process is:

$$T(t) = T0 + B1^2 * \Delta T * \left(1 - e^{-\frac{t}{\tau}}\right)$$

where t represents a current scanned duration, T(t) represents a current temperature of the surface temperature of the local coil, T0 represents an initial temperature of the surface temperature of the local coil, B1 represents the intensity of the B1 field, ΔT represents a temperature difference between the thermal equilibrium temperature of the surface temperature of the local coil and the initial temperature of the surface temperature of the local coil when the local coil is placed at the set position in the inspection bore of the MR scanner and the intensity of the B1 field is one µT, and τ represents a scanning duration required for the surface temperature of the local coil to reach 0.632ΔT when the local coil is placed at the set position in the inspection bore of the MR scanner and the intensity of the B1 field is one µT.

In an optional embodiment, the obtaining, by the B1 field second-intensity obtaining module 92, of a second intensity of the B1 field that is required for the surface temperature of the local coil to increase by heating to the maximum safety temperature within a set total MR scanning duration when the local coil is placed at the set position includes:

$$(B1_{short})^2 = (B1_{infinite})^2 * \frac{1}{1 - e^{-\frac{t_{scan}}{\tau}}}$$

where $B1_{short}$ represents the second intensity of the B1 field, $B1_{infinite}$ represents the first intensity of the B1 field, and $t_{scan}$ represents the set total MR scanning duration.

In an optional embodiment, the determining, by the B1 field second-intensity obtaining module 92 based on the second intensity of the B1 field, of a third intensity of the B1 field that is required when MR scanning is performed for the set total MR scanning duration includes: when only one scanning protocol is used within the set total MR scanning duration, using the third intensity of the B1 field as an intensity of the B1 field that corresponds to the scanning protocol.

In an optional embodiment, the determining, by the B1 field second-intensity obtaining module 92 based on the second intensity of the B1 field, of a third intensity of the B1 field that is required when MR scanning is performed for the set total MR scanning duration includes: when a plurality of scanning protocols are used within the set total MR scanning duration and a scanning duration for each scanning protocol is the same, using the third intensity of the B1 field as a sum of intensities of the B1 field that correspond to all the scanning protocols, where an intensity of the B1 field that corresponds to the $n^{th}$ scanning protocol is:

$$(B1_{protocoln})^2 = \left(\frac{1}{2}\right)^n * (B1'_{short})^2,$$

where $B1_{protocoln}$ represents the intensity of the B1 field that corresponds to the $n^{th}$ scanning protocol, and $B1_{short}'$ represents the third intensity of the B1 field, where 1≤n≤N, and N represents a total number of scanning protocols used within the set total MR scanning duration.

In an optional embodiment, the determining, by the B1 field second-intensity obtaining module 92 based on the second intensity of the B1 field, of a third intensity of the B1 field that is required when MR scanning is performed for the set total MR scanning duration includes: when a plurality of scanning protocols are used within the set total MR scanning duration and a scanning duration for each scanning protocol is not completely the same, using the third intensity of the B1 field as a sum of intensities of the B1 field that correspond to all the scanning protocols, where an intensity of the B1 field that corresponds to the $n^{th}$ scanning protocol is:

$$(B1_{protocoln})^2 = \frac{\left(\frac{1}{2}\right)^n * (B1'_{short})^2 * t_{single\_protocol}}{t_{protocoln}}$$

where $B1_{protocoln}$ represents the intensity of the B1 field that corresponds to the $n^{th}$ scanning protocol, $B1_{short}'$ represents the third intensity of the B1 field, $t_{single\_protocol}$ represents a set standard scanning duration for a single scanning protocol, and $t_{protocoln}$ represents an actual scanning duration for the $n^{th}$ scanning protocol, where 1≤n≤N, and N represents a total number of scanning protocols used within the set total MR scanning duration.

In an optional embodiment, the determining, by the B1 field second-intensity obtaining module 92 based on the second intensity of the B1 field, of a third intensity of the B1 field that is required when MR scanning is performed for the set total MR scanning duration includes: when a plurality of different types of scanning sequences are used within the set total MR scanning duration, obtaining an intensity of the B1 field that is used for each scanning sequence through the following steps A and B:

A. performing initialization m=1, and calculating:

$$(B1\_limit_m)^2 = \min\left\{\left(\frac{1}{2}\right)^m * (B1_{single\_protocol})^2, (B1_{SAR\_limit})^2\right\}$$

where:

$$(B1_{single\_protocol})^2 = (B1_{infinite})^2 * \frac{1}{1 - e^{-\frac{t_{single\_protocol}}{\tau}}}$$

$$t_{allowed\_duration\_m} = \frac{(B1_{single\_protocol})^2}{(B1\_limit_m)^2} * t_{single\_protocol}$$

and calculating a maximum value that satisfies:

$$\sum_{p_m=1}^{p_m=P_m} t_{seq\_p_m} \leq t_{allowed\_duration\_m}$$

where the maximum value $P_m$ is the number of scanning sequences for which $B1\_limit_m$ is used as the intensity of the B1 field;

where:

$B1\_limit_m$ represents the $m^{th}$ intensity of the B1 field that is used during a current MR scanning process, $B1_{single\_protocol}$ represents an intensity of the B1 field that is for a single scanning protocol, $B1_{SAR\_limit}$ represents a preset SAR-based limit value of the intensity of the B1 field, $B1_{infinite}$ represents the first intensity of the B1 field, $t_{single\_protocol}$ represents a set standard scanning duration for a single scanning protocol, τ represents a scanning duration required for the surface temperature of the local coil to reach 0.632*(the thermal equilibrium temperature—an initial temperature of the surface temperature of the local coil) when the local coil is placed at the set position in the inspection bore of the MR scanner and the intensity of the B1 field is one μT, $t_{allowed\_duration\_m}$ represents an upper limit of a scanning duration for the $m^{th}$ intensity of the B1 field, $p_m$ represents a sequence number of the $p^{th}$ scanning sequence in all scanning sequences for which $B1\_limit_m$ is used as the intensity of the B1 field during the current MR scanning process, $P_m$ represents the number of scanning sequences for which $B1\_limit_m$ is used as the intensity of the B1 field during the current MR scanning process, and $t_{seq\_p_m}$ represents a scanning duration for the $p^{th}$ scanning sequence in all scanning sequences for which $B1\_limit_m$ is used as the intensity of the B1 field during the current MR scanning process;

B. letting m=m+1, and returning to step A until:

$\Sigma P_m \geq P$ where P represents a total number of scanning sequences used during the current MR scanning process.

An embodiment of the present disclosure further provides an MR scanner, including the apparatus 90 for limiting a B1 field in MRI.

The embodiments above are merely preferred embodiments of the present disclosure, which are not intended to limit it. Any amendments, equivalent substitutions or improvements etc. made within the spirit and principles of the present disclosure shall be included in the scope of protection thereof.

The various components described herein may be referred to as "modules." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to store and/or execute instructions or computer programs that are stored on a suitable computer-readable medium. Alternatively, the modules may themselves be part of a computer-readable medium and store respective computer-executable instructions thereon.

What is claimed is:

1. A method for limiting a B1 field used for magnetic resonance imaging (MRI), comprising:
   obtaining a first intensity of the B1 field that is required for a thermal equilibrium temperature of a surface temperature of a local coil to be a maximum safety temperature when the local coil is placed at a predetermined position in a bore of a magnetic resonance (MR) scanner;
   obtaining, based on (i) the first intensity of the B1 field, and (ii) a relationship between the surface temperature of the local coil and a scanning duration and an intensity of the B1 field during an MR scanning process, a second intensity of the B1 field that is required for the surface temperature of the local coil to increase by heating to the maximum safety temperature within a predetermined total MR scanning duration when the local coil is placed at the predetermined position; and
   determining, based on the second intensity of the B1 field, a third intensity of the B1 field that is required when MR scanning is performed for the predetermined total MR scanning duration,
   wherein the third intensity of the B1 field is not greater than the second intensity of the B1 field.

2. The method according to claim 1, wherein the predetermined position in the bore of the MR scanner is a highest point of an inner bore wall of the MR scanner.

3. The method according to claim 1, further comprising:
   prior to obtaining the first intensity of the B1 field, when the local coil is placed at the predetermined position and the intensity of the B1 field is one μT, obtaining a temperature difference between the thermal equilibrium temperature of the surface temperature of the local coil and an initial temperature of the surface temperature of the local coil, and setting the temperature difference as a first temperature difference,
   wherein the obtaining of the first intensity of the B1 field comprises:
      when the local coil is placed at the predetermined position in the bore of the MR scanner and the thermal equilibrium temperature of the surface temperature of the local coil is the maximum safety temperature, obtaining a temperature difference between the maximum safety temperature and the initial temperature of the surface temperature of the local coil, and setting the temperature difference as a second temperature difference;
      dividing the second temperature difference by the first temperature difference; and
      using an obtained quotient as a squared value of the first intensity of the B1 field.

4. The method according to claim 1, wherein the relationship between the surface temperature of the local coil and the scanning duration and the intensity of the B1 field during the MR scanning process is represented as:

$$T(t) = T0 + B1^2 * \Delta T * \left(1 - e^{-\frac{t}{\tau}}\right),$$

wherein:
   t represents a current scanned duration,
   T(t) represents a current temperature of the surface temperature of the local coil,
   T0 represents an initial temperature of the surface temperature of the local coil,
   B1 represents the intensity of the B1 field,
   ΔT represents a temperature difference between the thermal equilibrium temperature of the surface temperature of the local coil and the initial temperature of the surface temperature of the local coil when the local coil is placed at the predetermined position in the bore of the MR scanner and the intensity of the B1 field is one μT, and
   τ represents a scanning duration required for the surface temperature of the local coil to reach 0.632ΔT when the local coil is placed at the predetermined position in the bore of the MR scanner and the intensity of the B1 field is one μT.

5. The method according to claim 4, further comprising:
   obtaining the second intensity of the B1 field that is required for the surface temperature of the local coil to increase by heating to the maximum safety temperature within a predetermined total MR scanning duration when the local coil is placed at the predetermined position in accordance with the following relationship:

$$(B1_{short})^2 = (B1_{infinite})^2 * \frac{1}{1 - e^{-\frac{t_{scan}}{\tau}}},$$

wherein:
- $B1_{short}$ represents the second intensity of the B1 field,
- $B1_{infinite}$ represents the first intensity of the B1 field, and
- $t_{scan}$ represents the predetermined total MR scanning duration.

6. The method according to claim 1, wherein the determining of the third intensity of the B1 field comprises:
when only one scanning protocol is used within the predetermined total MR scanning duration, determining the third intensity of the B1 field as an intensity of the B1 field that corresponds to the scanning protocol.

7. The method according to claim 1, wherein the determining of the third intensity of the B1 field comprises:
when a plurality of scanning protocols are used within the predetermined total MR scanning duration and a scanning duration for each scanning protocol is the same as one another, determining the third intensity of the B1 field as a sum of intensities of the B1 field from each of the plurality of the scanning protocols,
wherein an intensity of the B1 field that corresponds to an $n^{th}$ scanning protocol from among the plurality of scanning protocols is represented as:

$$(B1_{protocoln})^2 = \left(\frac{1}{2}\right)^n * (B1'_{short})^2,$$

and wherein:
- $B1_{protocoln}$ represents the intensity of the B1 field that corresponds to the $n^{th}$ scanning protocol,
- $B1_{short}'$ represents the third intensity of the B1 field,
- $1 \leq n \leq N$, and
- N represents a total number of the plurality of scanning protocols used within the predetermined total MR scanning duration.

8. The method according to claim 1, wherein the determining of the third intensity of the B1 field comprises:
when a plurality of scanning protocols are used within the predetermined total MR scanning duration and a scanning duration for each scanning protocol is not the same as one another, determining the third intensity of the B1 field as a sum of intensities of the B1 field of the plurality of scanning protocols,
wherein an intensity of the B1 field that corresponds to an $n^{th}$ scanning protocol of the plurality of scanning protocols is represented as:

$$(B1_{protocoln})^2 = \frac{\left(\frac{1}{2}\right)^n * (B1'_{short})^2 * t_{single\_protocol}}{t_{protocoln}},$$

wherein:
- $B1_{protocoln}$ represents the intensity of the B1 field that corresponds to the $n^{th}$ scanning protocol,
- $B1_{short}'$ represents the third intensity of the B1 field,
- $t_{single\_protocol}$ represents a predetermined standard scanning duration for a single scanning protocol,
- $t_{protocoln}$ represents a scanning duration for the $n^{th}$ scanning protocol,
- $1 \leq n \leq N$, and
- N represents a total number of the plurality of scanning protocols used within the predetermined total MR scanning duration.

9. The method according to claim 1, wherein the determining of the third intensity of the B1 field comprises:
when a plurality of different types of scanning sequences are used within the predetermined total MR scanning duration, obtaining, through the following steps A and B, an intensity of a respective B1 field that is used for each one of the plurality of different types of scanning sequences:

A. performing an initialization m=1, and calculating:

$$(B1\_limit_m)^2 = \min\left\{\left(\frac{1}{2}\right)^m * \left(B1_{B1_{single\_protocol}}\right)^2, (B1_{SAR\_limit})^2\right\}$$

wherein:

$$(B1_{single\_protocol})^2 = (B1_{infinite})^2 * \frac{1}{1 - e^{-\frac{t_{single\_protocol}}{\tau}}}$$

$$t_{allowed\_duration\_m} = \frac{(B1_{single\_protocol})^2}{(B1\_limit_m)^2} * t_{single\_protocol};$$

a maximum value $P_m$ that satisfies:

$$\sum_{p_m=1}^{p_m=P_m} t_{seq\_p_m} \leq t_{allowed\_duration\_m},$$

wherein:
- the maximum value $P_m$ represents a number of scanning sequences for which $B1\_limit_m$ is used as the intensity of the B1 field,
- $B1\_limit_m$ represents the $m^{th}$ intensity of the B1 field that is used during a current MR scanning process,
- $B1_{single\_protocol}$ represents an intensity of the B1 field that is for a single scanning protocol,
- $B1_{SAR\_limit}$ represents a predetermined limit value of the intensity of the B1 field,
- $B1_{infinite}$ represents the first intensity of the B1 field,
- $t_{single\_protocol}$ represents a predetermined standard scanning duration for a single scanning protocol,
- $\tau$ represents a scanning duration required for the surface temperature of the local coil to reach 0.632*(the thermal equilibrium temperature–an initial temperature of the surface temperature of the local coil) when the local coil is placed at the predetermined position in the bore of the MR scanner and the intensity of the B1 field is one µT,
- $t_{allowed\_duration\_m}$ represents an upper limit of a scanning duration for the $m^{th}$ intensity of the B1 field,
- $p_m$ represents a sequence number of the $p^{th}$ scanning sequence in all scanning sequences for which $B1\_limit_m$ is used as the intensity of the B1 field in the current MR scanning process,
- $P_m$ represents the number of scanning sequences for which $B1\_limit_m$ is used as the intensity of the B1 field in the current MR scanning process, and
- $t_{seq\_p_m}$ represents a scanning duration for the $p^{th}$ scanning sequence in all scanning sequences for which $B1\_limit_m$ is used as the intensity of the B1 field during the current MR scanning process;

B. letting m=m+1, and returning to step A until:
$\Sigma P_m \geq P$, wherein P represents a total number of scanning sequences used during the current MR scanning process.

10. An apparatus for limiting a B1 field used for magnetic resonance imaging (MRI), comprising:

a computer readable medium having instructions stored thereon; and a processor configured to execute the instructions stored on the computer-readable medium to cause the apparatus to:

obtain a first intensity of a B1 field that is required for a thermal equilibrium temperature of a surface temperature of a local coil to be a maximum safety temperature when the local coil is placed at a predetermined position in a bore of a magnetic resonance (MR) scanner; and obtain, based on (i) the first intensity of the B1 field, and (ii) a relationship between the surface temperature of the local coil and a scanning duration and an intensity of the B1 field during an MR scanning process, a second intensity of the B1 field that is required for the local coil to be heated to the maximum safety temperature within a predetermined total MR scanning duration when the local coil is placed at the predetermined position; and determine, based on the second intensity of the B1 field, a third intensity of the B1 field that is required when MR scanning is performed for the predetermined total MR scanning duration, wherein the third intensity of the B1 field is not greater than the second intensity of the B1 field.

* * * * *